(12) United States Patent
Parker

(10) Patent No.: US 6,355,826 B1
(45) Date of Patent: Mar. 12, 2002

(54) SYNTHESIS OF STABLE NITRILE OXIDE COMPOUNDS

(75) Inventor: Dane Kenton Parker, Massillon, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/603,590

(22) Filed: Jun. 26, 2000

Related U.S. Application Data

(62) Division of application No. 09/136,754, filed on Aug. 19, 1998, now abandoned.
(60) Provisional application No. 60/059,108, filed on Sep. 17, 1997.

(51) Int. Cl.$^7$ ............................................. C07C 291/06
(52) U.S. Cl. ...................................................... 558/299
(58) Field of Search ......................................... 558/299

(56) References Cited

U.S. PATENT DOCUMENTS

| | | | | |
|---|---|---|---|---|
| 2,974,120 A | * | 3/1961 | Miller | .......................... 524/95 |
| 3,258,397 A | * | 6/1966 | Hess et al. | ............... 558/299 X |
| 3,390,204 A | | 6/1968 | Breslow | ...................... 260/837 |
| 3,931,106 A | * | 1/1976 | Crosby et al. | ............... 525/371 |
| 4,751,271 A | * | 6/1988 | Graves | ..................... 525/329.3 |
| 4,762,870 A | * | 8/1988 | Graves et al. | ................. 524/93 |
| 4,778,857 A | * | 10/1988 | Graves et al. | ............... 525/375 |
| 4,975,497 A | * | 12/1990 | Tate et al. | ................... 525/375 |
| 5,001,171 A | * | 3/1991 | Bohm et al. | ................. 523/206 |
| 5,710,290 A | * | 1/1998 | Lysenko et al. | ............. 549/513 |

FOREIGN PATENT DOCUMENTS

| | | | | |
|---|---|---|---|---|
| SU | 1825829 | 1/1991 | ........ | D06M/15/643 |
| SU | 1824389 | 6/1993 | ......... | C07C/47/544 |
| SU | 2042664 | 8/1995 | ......... | C07C/291/06 |

OTHER PUBLICATIONS

Database WPI Section Ch, Week 199619 Derwent Publication Ltd., London, GB; AN 1996–186753 XP002126858, & RU 2 042 664 C (Borodachev I V), Aug. 27, 1995 (1995–08–27).

Hanhela, Peter J. Et Al: "Synthesis and stability of aryl bis(nitrile oxides) with potential as curing agents for polysulfide sealants" Aust. J. Chem. (1989), 42(2), 287–99, XP00865671 p. 289 p. 90–p. 293 p. 295: "Naphtalene–1, 4–and –1,5–dicarbaldehydes . . . " and "Conversion of Bis(chloromethyl)naphtlenes into Dialdehydes . . . " p. 296: "Synthesis of Oximes".

D V Tsygnov: "Synthesis and properties of stable aromatic bis(nitrileoxides)" Bulletin of the Academy of Sciences of the USSR, Division of Chemical Science. vol. 40, No. 6, Dec. 20, 1991, pp. 1238–1243 XP002126857 p. 1239.

K B G Torssell, "Nitrile Oxides, Nitrones and Nitronates in Organic Synthesis," New York: VCH Publi, 1988.

Leonid I Belen'Kit et al, Tetrahedron, vol. 49, No. 16, pp. 3397–3404, 1993.

Christoph Grundmann and Reinhard Richter, "Preparation of the Dinitrile Oxide of Mesitylene, Preparation of the Dinitrile Oxide of Mesitylene," The Journal of Organic Chemistry, 33, 476 (1968).

V V Boiko, N D Malaya and L M Klimenko, "Rheological properties of solutions of diene elastomers with the mesitylene dinitrile oxide," International Polymer Science and Technology, vol. 20, No. 10, T51, 1993.

V V Boiko and I V Grinev, "Influence of MDNO/Processing Elastomers," International Polymer Science and Technology, vol. 22, No. 7, T/21, 1995.

Milton J Rhoad and Paul R. Flory, "Preparation of Bischloromethylmesitylene," Journal of the American Chemical Society, 72, 2216 (1950).

A W van der Made and R H van der Made, "Preparation of Bromomethylaromatic Compounds," The Journal of Organic Chemistry, 58, 1262 (1993).

* cited by examiner

*Primary Examiner*—Floyd D. Higel
(74) *Attorney, Agent, or Firm*—Alvin T. Rockhill

(57) ABSTRACT

This invention discloses a process for the synthesis of stable aryl nitrile oxides which comprises the sequential steps of (1) halomethylating a halomethyl group onto a substituted aromatic compounds wherein said halomethyl group is halomethylated onto a position that is ortho to at least one of the substituent groups on the substituted aromatic compound; (2) converting the ortho halomethylated-substituted aromatic compound into an ortho-substituted aromatic aldehyde by reacting the ortho halomethylated-substituted aromatic compound with a salt selected from the group consisting of sodium 2-nitropropane and potassium 2-nitropropane in a lower alcohol solvent; (3) converting the ortho-substituted aromatic aldehyde into an ortho-substituted aromatic; and (4) converting the ortho-substituted aromatic oxime into the ortho-substituted aryl nitrile oxide by reacting the ortho-substituted aromatic oxime with an aqueous sodium hypochlorite solution.

18 Claims, No Drawings

SYNTHESIS OF STABLE NITRILE OXIDE COMPOUNDS

This is a Divisional of application Ser. No. 09/136,754, filed on Aug. 19, 1998, now abandoned, which claims benefit of Provisional No. 60/059,108 filed Sep. 17,1997.

Nitrile oxide compounds are extremely reactive toward multiple bonds in organic compounds and polymers. This high level of reactivity allows for dinitrile oxides to cure (crosslink) olefin-containing polymers under very mild conditions. This invention discloses a process for the synthesis of stable aryl nitrile oxides which comprises the sequential steps of (1) halomethylating a halomethyl group onto a substituted aromatic compound having at least one substituent group selected from the group consisting of alkyl groups, aryl groups, fused aryl groups, alkaryl groups, halogen atoms, alkoxy groups and nitro groups, wherein said halomethyl group is halomethylated onto a position that is ortho to at least one of the substituent groups on the substituted aromatic compound; (2) converting the ortho halomethylated-substituted aromatic compound into an ortho-substituted aromatic aldehyde by reacting the ortho halomethylated-substituted aromatic compound with a salt selected from the group consisting of sodium 2-nitropropane and potassium 2-nitropropane in a lower alcohol solvent; (3) converting the ortho-substituted aromatic aldehyde into an ortho-substituted aromatic oxime by reacting the ortho-substituted aromatic aldehyde with hydroxylamine; and (4) converting the ortho-substituted aromatic oxime into the ortho-substituted aryl nitrile oxide by reacting the ortho-substituted aromatic oxime with an aqueous sodium hypochlorite solution at a temperature which is within the range of about −5° C. to about 20° C.

BACKGROUND OF THE INVENTION

Most nitrile oxides (RCNO) are little known, short-lived reactive species that are structurally isomeric with isocyanates (RNCO) and cyanates (ROCN). Being reactive, they readily undergo 1,3-dipolar additions with a great variety of multiple bond functional groups. The relative decreasing reactivity of nitrile oxides with these multiple bonds is roughly: C=S, N=N, P(V)=C>C=P(III), C=As, C=C, C=N, C=Se, B=N>C≡P, C≡C>P(V)=N, C≡N>C=O. In the absence of these functional groups, most nitrile oxides will readily dimerize to furoxans (1,2,5-oxadiazole-2-oxides).

Nitrile oxides are mild oxidants and will liberate iodine from solutions of potassium iodide. The nitrile oxide function imposes the same type of solubility characteristics on a molecule that a cyano group does. Aromatic nitrile oxides, especially those where the nitrile oxide is flanked by at least one and preferably two ortho groups have been found to be stable compounds. For example, 2,4,6-Trimethylbenznitrile oxide is a stable crystalline solid (m.p. 105–108° C.) with two characteristic strong IR absorptions at 2290 cm$^{-1}$ (—C≡N) and 1334 cm$^{-1}$ (≡N—O). In the C$^{13}$ NMR, the carbon in the —CNO group is found at 35.7 ppm compared with 117.5 ppm for the carbon in the corresponding nitrile compound. This implies that the carbon atom carries considerable negative charge whereas the oxygen bears a positive charge. This highly dipolar character explains their high reactivity toward multiple bonds, see K B G Torssell, "Nitrile Oxides, Nitrones and Nitronates in Organic Synthesis," New York: VCH Publ, 1988.

The history of using polyfunctional nitrile oxides or their precursors as crosslinking agents for unsaturated polymers appears to go back to at least 1968 when chemists from Hercules were granted U.S. Pat. No. 3,390,204 for this application. In most cases, the polyfunctional nitrile oxide itself was too unstable to use directly. In these cases, the polyfunctional hydroximoyl halides were used as stable precursors. When mixed with unsaturated elastomers and then exposed to a base such as triethylamine, the hydroximoyl halide function immediately dehydrohalogenates to produce the nitrile oxide group which then rapidly crosslinks the elastomer. The resulting unfilled crosslinked elastomers from styrene-butadiene rubber (SBR), polybutadiene rubber (PBd) and natural rubber (NR) were described as hard, tough and substantially insoluble in chloroform. The crosslinking system was also noted not to be affected by air or moisture. Oddly, this patent makes no mention of any actual cured physical properties or potential applications.

Because no practical system evolved from this work, we can assume it had serious drawbacks either in process control, cost, toxicity and/or ultimate physical properties. Obviously, a two-component system requiring both a hydroximoyl halide and an organic base is not desirable, whereas the use of polynitrile oxide compounds alone is limited only to those nitrile oxides whose stability is sufficient to allow their dispersion and reaction with rubber in preference to self-dimerization. As previously mentioned, very few stable nitrile oxides are known even today. What is known about this class of chemicals is that aromatic nitrile oxides with one or two ortho substituents have enhanced chemical stability with regard to dimerization resistance. Unfortunately, the prime precursors for such nitrile oxides are sterically hindered aromatic dialdehydes. Dialdehydes of this type are relatively difficult to prepare in good yields and purity and this lack of a good synthetic method probably accounts for the field's lack of development.

In 1989, the situation began to change when Russian chemists developed a novel approach to the synthesis of sterically hindered aromatic dialdehydes, see Leonid I Belen'kii et al, Tetrahedron, Vol 49, No 16, pages 3397–3404, 1993, and Russian Patent SU 4,750,502. With this new technique, aromatic hydrocarbons such as mesitylene or durene could be converted (in several steps) into dialdehydes in yields between 58 to 71 percent (based on hydrocarbon). This was a substantial improvement over the known technique of oxidizing bis-(hydroxymethyl) mesitylene to the dialdehyde with lead tetraacetate described by Christoph Grundmann and Reinhard Richter, "Preparation of the Dinitrile Oxide of Mesitylene," The Journal of Organic Chemistry, 33, 476 (1968).

Within a few years, another Russian group revisited the topic of rubber curing with dinitrile oxides. Only this time, they now had the dinitrile oxide of mesitylene (MDNO) readily available because of the new dialdehyde synthesis, see V V Boiko, N D Malaya and L M Klimenko, "Rheological properties of solutions of diene elastomers with the mesitylene dinitrile oxide," International Polymer Science and Technology, Vol 20, No 10, T51, 1993. In their initial studies, they investigated the change in viscosity of various elastomer solutions as a function of time, temperature and MDNO concentration. Polymer solutions evaluated were cis-polyisoprene, polybutadiene, SBR and NBR. The relative rate of gelation was PBd>SER≡NBR>IR. With PBd and two parts of MDNO, solution gelation tot place in 1.5 hours at 25° C.; 0.5 hours at 40° C. From this work, they concluded that MDNO could be used as an efficient low-temperature vulcanizing agent for a wide variety of diene elastomers. More recent work by the same Russian group using MDNC and various diene elastomers showed the same order of reactivity as measured by Mooney viscosity increases during mixing, see V V Boiko and I V Grinev, "Influence of MDNO/Processing Elastomers," International Polymer Science and Technology, Vol 22, No 7, T/21, 1995.

The first practical application of this technology appears to be described in Russian Patent SU 1, 825,829-A1 to the Ukranian Textile Industry Research Institute. In this patent, polymethyl-vinyl-siloxane rubber having a M.W. of 500,000 and a molar olefin content of 0.45–0.55 percent was crosslinked with MDNO in ethyl acetate on a fabric.

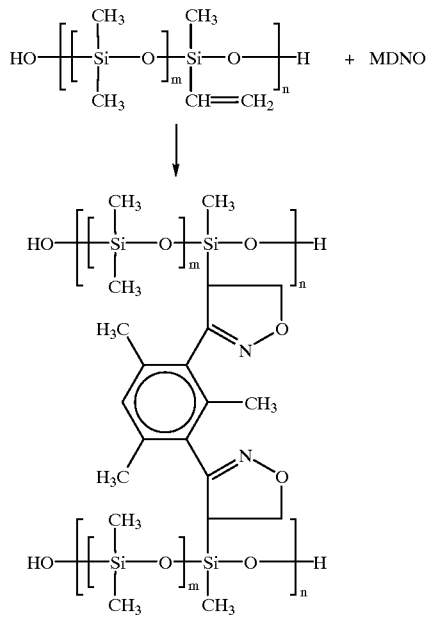

The crosslinked fabric treatment produced a durable water and dirt repellent finish. Russian Patent SU 1,824,389-A1 has also been issued to the Ukrainian Textile Industry Research Institute for the synthesis of 2,4,5-trimethylbenzene-1,3-dialdehyde as an intermediate to the corresponding dinitrile oxide as a low temperature hardener.

Russian Patent 2,042,664-C1 describes a new synthesis for dialkylbenzene dinitrile oxides and demonstrated their utility for curing rubbers with low levels of unsaturation at low temperature. Whereas, MDNO has its nitrile oxide groups each flanked by two methyl groups, the new dinitrile oxide compounds have each —CNQ group flanked by only one alkyl group. It is not clear, however, whether or not this structural difference would result in different rates of cure since a comparison control with MDNO was not included in the cured rubber physical property data. Nevertheless, a comparison of the room temperature cured properties of several low unsaturation polymers with the same polymers cured with conventional high temperature sulfur or peroxide systems, showed remarkable similarity.

The starting materials for this new synthesis are meta or para-dimethyl- or meta or para-diethylbenzene. The hydrocarbons are treated with specific molar ratios of aqueous formaldehyde solution, hydrochloric acid, sulfuric acid and acetic acid at 70–85° C. to prepare bis-(chloromethyl)-dialkylbenzenes (see Milton J Rhoad and Paul J Flory, "Preparation of Bischloromethylmesitylene," Journal of the American Chemical Society, 72, 2216 (1950)). After cooling to 15–25° C., crystals of the bis-chloromethyl compounds are then filtered off, washed with water and dried In the next step, the bis-chloromethyl compounds are treated with an aqueous solution of hexamethylenetetramine in acetic acid for 4 hours at 95–100° C. The organic products (dialdehydes) were then extracted from the reaction mixture with carbon tetrachloride. After water-washing the carbon tetrachloride solution, an aqueous solution of hydroxylamine hydrochloride was added followed by the addition of an aqueous NaOH solution to generate free hydroxylamine.

The organic layer was then separated after about 1 hour at 25–35° C. The aqueous layer was cooled to 20° C. and neutralized to pH 7 with HCl to precipitate the dioxime. The dioxime is filtered off, washed with water and dried.

Treatment of the dioxime with acidified sodium hypochlorite solution at −10 to 0° C. gave the crystalline dinitrile oxide compound in very good yields.

Although this synthesis is a great improvement over previous methods, it does have several drawbacks such as the use of a chlorinated solvent and multiple extractions. Additionally, the hexamethylenetetramine/acetic acid method for conversion of the chloromethyl group into an aldehyde is not synthetically useful for the conversion of more highly hindered halomethyl groups such as those found in halomethylated mesitylene.

A W van der Made and R H van der Made, "Preparation of Bromomethylaromatic Compounds," The Journal of Organic Chemistry, 58, 1262 (1993) reports that mesitylene and other structurally similar aromatic compounds can be efficiently bis-bromomethylated in high yields using readily available reagents.

SUMMARY OF THE INVENTION

The new synthesis technique of this invention does not use chlorinated solvents or hexamethylenetetramine and can readily convert even a relatively hindered halomethyl group to an aldehyde function in high yield. The overall yield from mesitylene to mesitylene dinitrile oxide by the process of this invention is also higher than that achieved by other known procedures (67 percent versus 50 percent).

The stable nitrile oxide compounds synthesized by utilizing the techniques of this invention can be utilized in a wide variety of applications. For instance, stable nitrile oxide compounds can be used in step-growth polymerization, adhesives, polymer modification and curing rubber.

There are relatively few chemical reactions known that can modify a diene rubber selectively and at low temperature the way nitrile oxides can. This almost unique ability offers many interesting possibilities for polymer modification. One such possibility is the use of a mono-nitrile oxide as a coupling agent between rubber and carbon black. Although the mechanism of this interaction is unknown, Japanese chemists demonstrated that diene rubbers containing either isoxazolidine groups (from nitrone addition to rubber) or isoxazoline groups (from nitrile oxide addition to rubber) greatly enhance the cured tensile properties of filled PBd compounds (see K Tada, Y Numata and T Katsumura, "Modified Polybutadiene by 1,3-Diphenylnitrone and Nitrile Oxides," Journal of Applied Polymer Science, 15, 117 (1971).

Because dinitrile oxides are extremely reactive toward double bonds, including the carbon-carbon double bonds in rubbers, they can be employed as a curing (crosslinking) agents for rubbers. Dinitrile oxides are especially suitable for curing coatings or "vulcanizing" latex because they will cure or crosslink the olefin-containing polymers under very mild conditions, such as at room temperature.

This invention more specifically discloses a process for the synthesis of stable aryl nitrile oxides which comprises the sequential steps of (1) halomethylating a halomethyl group onto a substituted aromatic compound having at least one substituent group selected from the group consisting of alkyl groups, aryl groups, fused aryl groups, alkaryl groups, halogen atoms, alkoxy groups and nitro groups, wherein said halomethyl group is halomethylated onto a position that is ortho to at least one of the substituent groups on the substituted aromatic compound to produce an ortho halomethylated-substituted aromatic compound; (2) converting the ortho halomethylated-substituted aromatic compound into an ortho-substituted aromatic aldehyde by reacting the ortho halomethylated-substituted aromatic compound with a salt selected from the group consisting of sodium 2-nitropropane and potassium 2-nitropropane in a lower alcohol solvent; (3) converting the ortho-substituted aromatic aldehyde into an ortho-substituted aromatic oxime by reacting the ortho-substituted aromatic aldehyde with hydroxylamine; and (4) converting the ortho-substituted aromatic oxime into the ortho-substituted aryl nitrile oxide by reacting the ortho-substituted aromatic oxime with an aqueous sodium hypochlorite solution at a temperature which is within the range of about −5° C. to about 20° C.

DETAILED DESCRIPTION OF THE INVENTION

In the first step of the process of this invention, a halomethyl group is halomethylated onto a substituted aromatic compound. The substituted aromatic compound will contain at least one alkyl substituent group, aryl substituent group, fused aryl substituent group, alkaryl substituent group, halogen substituent group, alkoxy substituent group or nitro substituent group. In this step, the halomethyl group is halomethylated onto a position that is ortho to at least one of the substituent groups on the substituted aromatic compound. As a specific example, in the case of naphthalene, the halomethyl group is halomethylated onto a position that is ortho to the fused aryl group (benzene ring) as shown below:

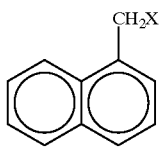

wherein X represents a halogen atom.

A wide variety of substituted aromatic compounds can be utilized as the starting material. These substituted aromatic compounds will contain at least one alkyl, aryl, fused aryl, alkaryl, halogen, alkoxy or nitro substituent group. Some representative examples of substituted aromatic compounds that can be used include: 1,3,5-trimethylbenzene (mesitylene), 1,2,4,5-tetramethylbenzene (durene), toluene, o-xylene, m-xylene, p-xylene, pseudocumene, isodurene, prehnitene, 1,3-dimethyl-5-t-butylbenzene, 1,3,5-triethylbenzene, 1,3,5-tripropylbenzene, naphthalene, anthracene, α-methylnaphthalene, β-methylnaphthalene, phenanthrene, 1,2-benzanthracene, p-dichlorobenzene, o-chlorotoluene, p-chlorotoluene, p-bromotoluene, bromodurene, bromoisodurene, bromoprehnitene, bromomesitylene, 1-chloro-1-mesitylethylene, p-bromoethylbenzene, 1-chloro-1-mesitylpropene, α-chloroisodurene, p-nitrotoluene, 1-nitronaphthalene, 1,4-diethoxybenzene, 1-ethoxy-4-nitronaphthalene, 1,4-dipropoxybenzene, 1,4-dibutoxybenzene, 1,4-diamyloxybenzene, 2,5-dimethoxytoluene, 2,5-dimethoxyoctylbenzene, 2,5-dimethoxybromobenzene, 3,-chloromethyl-1,2-dimethoxybenzene, 4-(β-chloropropyl)-1,2-dimethoxybenzene, 2,3,4-trimethoxybromobenzene, trimethoxy-p-xylene, 5-propyl-1:3-benzodioxole, and the like. Mesitylene and durene are preferred substituted aromatic compounds.

This halomethylation reaction can be carried out by reacting the substituted aromatic compound with a mixture of acetic acid, hydrogen bromide and paraformaldehyde at a temperature which is within the range of about 50° C. to about 120° C. For instance, one mole of the substituted aromatic compound (mesitylene) can be reacted with about two moles of the hydrogen bromide and about two moles of the paraformaldehyde. It is typically preferred from this reaction to be carried out at a temperature which is within the range of about 80° C. to about 95° C.

The halomethylation reaction can, in the alternative, be carried out by utilizing the procedure described by Milton J Rhoad and Paul J Flory, "The Synthesis of Polymeric Ethers," Journal of the American Chemical Society, Vol 72, page 2216 (1950), the teachings of which are incorporated herein by reference in their entirety. In this procedure, 50 grams (0.37 mole) of durene (melting point of 79° C. to 81° C.) dissolved in 200 ml (1.5 moles) of 40 percent aqueous formaldehyde and 100 ml. of concentrated hydrochloric acid were heated with stirring on a steam bath while a slow stream of hydrogen chloride gas was bubbled through the mixture. After six hours, the oil layer was separated while hot and set aside to cool. The fine white needles of crude product which deposited where collected, leaving the intermediate monochloromethyldurene in solution. The liquor was treated with a fresh formaldehyde-hydrochloric acid mixture as described above and an additional amount of crude product was obtained. A total of six such treatments of the original durene solution yielded 69 grams (80 percent) of crude bis-(chloromethyl)-durene. A single recrystallization from benzene gave 58 grams (67 percent). The product obtained had a melting point of 193–194° C.

In the second step of the process of this invention, the ortho halomethylated-substituted aromatic compound is converted into an ortho-substituted aromatic aldehyde by reacting the ortho halomethylated-substituted aromatic compound with a salt of 2-nitropropane. The salt of 2-nitropropane will typically be a sodium or potassium salt. This step is carried out, utilizing a lower alcohol as the solvent. The lower alcohol will typically contain from 1 to 5 carbon atoms. Some representative examples of alcohols that can be employed as the solvent include methanol, ethanol, n-propyl alcohol, isopropyl alcohol, n-butyl alcohol, isobutyl alcohol, t-butyl alcohol and n-pentyl alcohol. This reaction step will typically be carried out at a temperature that is within the range of about 20° C. to about 100° C. It is normally preferred for this reaction to be conducted at a temperature which is within the range of about 30° C. to 90° C., with temperatures in the range of 40° C. to 85° C. being most preferred.

In the third step of the process of this invention, the ortho-substituted aromatic aldehyde is converted into an ortho-substituted aromatic oxime by reacting the ortho-substituted aromatic aldehyde with hydroxylamine. This reaction step can be carried out in the same reaction vessel in which the ortho-substituted aromatic aldehyde was synthesized or the ortho-substituted aromatic aldehyde can be isolated and reacted with the hydroxylamine in a separate reaction vessel. This reaction step will typically be carried out at a temperature which is within the range of about 20° C. to 100° C. Reaction temperatures in the range of 30° C. to 70° C. are preferred, with temperatures within the range of 35° C. to 55° C. being most preferred.

In the final step of the process of this invention, the ortho-substituted aromatic oxime is converted into an ortho-substituted aromatic nitrile oxide or ortho-substituted aromatic dinitrile oxide by reacting it with an aqueous sodium hypochlorite (bleach) solution. It is normally preferred to utilize a solution that contains from about 4 weight percent to about 6 weight percent sodium hypochlorite. This reaction step will typically be carried out at a temperature which is within the range of about $-5°$ C. to $20°$ C.

As has been explained, the technique of this invention can be utilized to convert a wide variety of substituted aromatic compounds into stable nitrile oxide compounds, such as ortho-substituted aryl mononitrile oxides and ortho-substituted aryl dinitrile oxides. The following reaction is representative of conversions of a substituted aromatic compound into a stable nitrile oxide that can be carried out utilizing the techniques of this invention:

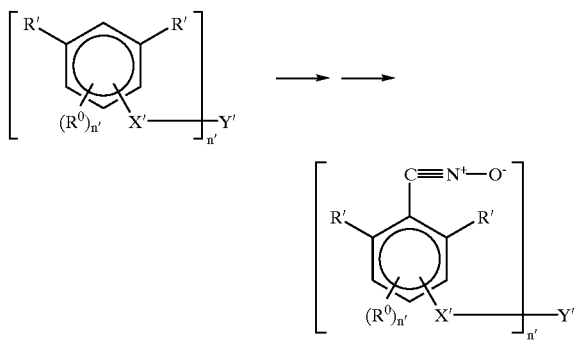

wherein each $R^1$ is independently $C_1$–$C_{12}$-alkyl, F, Cl, Br, I, O—$C_1$–$C_{12}$-alkyl or S—$C_1$–$C_{12}$-alkyl; each $R^0$ is a substituent that does not spontaneously react with the nitrile oxide group; each n' is independently 0, 1 or 2; n'' is an integer greater than 1; each X' is independently a bond or a connecting group; and Y' is a polyvalent radical containing an ether, ester, amide, amine, carbonate, ketone, urethane, arylene or thioether moiety; or each X' and Y' together are a bond connecting the benzene rings.

The following reactions are also representative of the conversion of various types of substituted aromatic compounds into stable nitrile oxides:

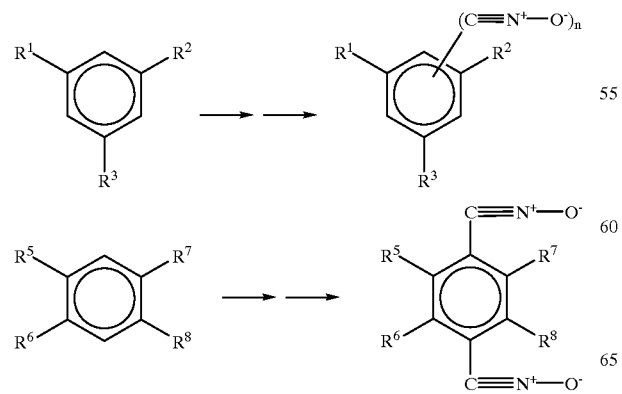

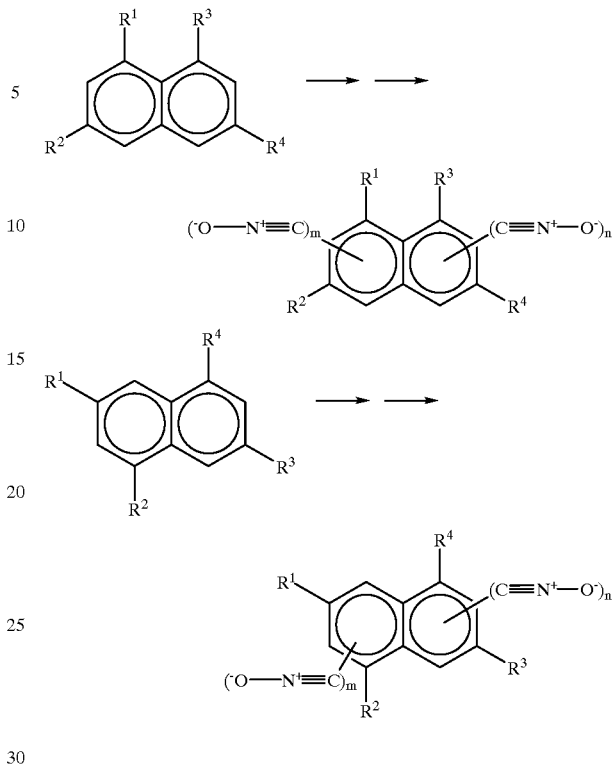

where $R^1$, $R^2$, $R^3$ and $R^4$ are each independently H, R, halo, SH, SR, SOR, $SO_2R$, hydroxy or OR, with the proviso that at least one of $R^1$, $R^2$, $R^3$ and $R^4$ that is adjacent to a nitrile oxide group is not H; $R^5$, $R^6$, $R^7$ and $R^8$ are each independently H, R, halo, S—H, SR, SOR, $SO_2R$, hydroxy or OR, wherein R is a $C_1$–$C_{12}$ linear, branched or cyclic alkyl group, preferably a $C_1$–$C_4$ linear or branched alkyl group, more preferably ethyl or methyl; or $R^5$ and $R^6$ or $R^7$ and $R^8$, together with the carbon atoms to which they are attached, form a benzene ring, wherein at least one of $R^5$ or $R^7$ is not H, and at least one of $R^6$ or $R^8$ is not H; i is 2 or 3; m and n are each 0, 1 or 2 and n+m$\geq$2, preferably 2 or 3.

The following reactions are also representative of the conversions of various types of substituted aromatic compounds into stable nitrile oxides:

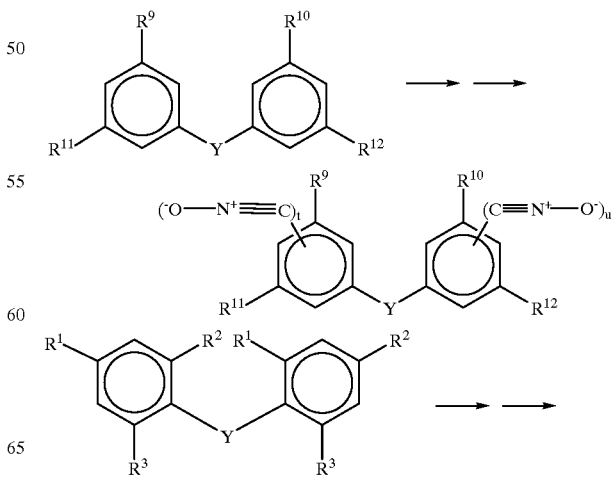

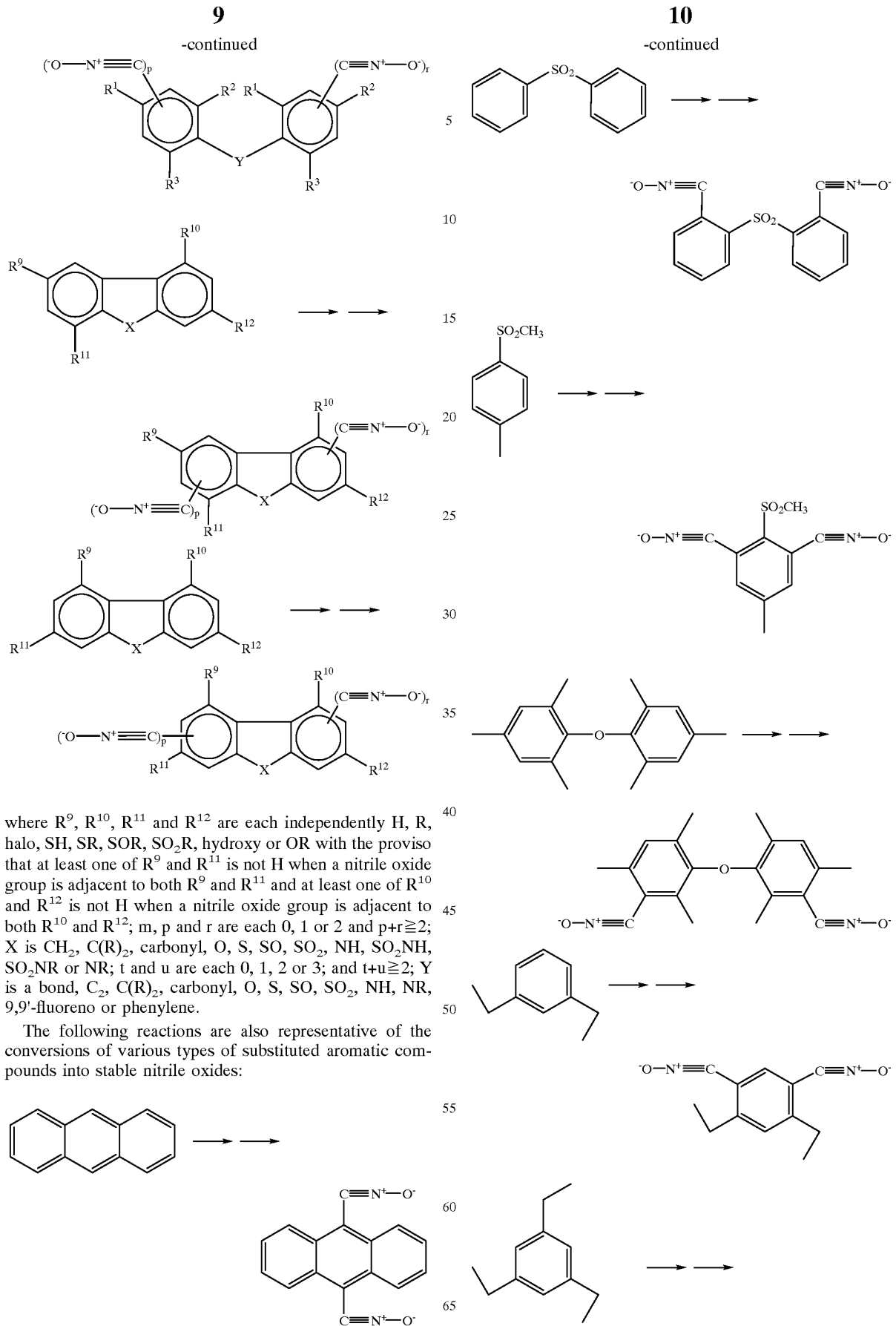

where $R^9$, $R^{10}$, $R^{11}$ and $R^{12}$ are each independently H, R, halo, SH, SR, SOR, $SO_2R$, hydroxy or OR with the proviso that at least one of $R^9$ and $R^{11}$ is not H when a nitrile oxide group is adjacent to both $R^9$ and $R^{11}$ and at least one of $R^{10}$ and $R^{12}$ is not H when a nitrile oxide group is adjacent to both $R^{10}$ and $R^{12}$; m, p and r are each 0, 1 or 2 and p+r≧2; X is $CH_2$, $C(R)_2$, carbonyl, O, S, SO, $SO_2$, NH, $SO_2NH$, $SO_2NR$ or NR; t and u are each 0, 1, 2 or 3; and t+u≧2; Y is a bond, $C_2$, $C(R)_2$, carbonyl, O, S, SO, $SO_2$, NH, NR, 9,9'-fluoreno or phenylene.

The following reactions are also representative of the conversions of various types of substituted aromatic compounds into stable nitrile oxides:

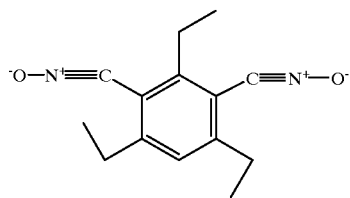

This invention is illustrated by the following examples which are merely for the purpose of illustration and are not to be regarded as limiting the scope of the invention or the manner in which it can be practiced. Unless specifically indicated otherwise, all parts and percentages are given by weight.

EXAMPLE 1 in this experiment, mesitylene dinitrile oxide (MDNO) was synthesized utilizing the technique of this invention. In the first step of the procedure used, mesitylene was halomethylated to produce 1,3-bis (bromomethyl)-2,4,6-trimethylbenzene. This is reaction can be depicted as follows:

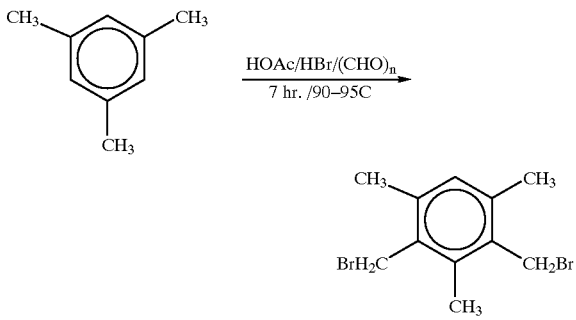

In conducting this reaction, a 2-liter three-necked round-bottomed flask equipped with a mechanical stirrer, condenser and not thermometer was charged with 96.0 g (0.80 moles) of 98 percent pure mesitylene (Aldrich), 51.79 g (ca. 1.6 moles) of 95 percent pure paraformaldehyde (Aldrich), 200 ml of glacial acetic acid and 433 g (320 ml) (1.6 moles) of 30 percent hydrogen bromide (HBr) in acetic acid solution (Aldrich). The mixture was slowly heated with stirring to 90–95° C. and held at this temperature for 7 hours.

After several hours heating, product dibromide compound begins to precipitate from the reaction mixture. The mixture was allowed to stand at room temperature overnight. The crystalline mass was then broken up and stirred to form a uniform slurry before adding 1 liter of tap water to complete the precipitation. The product was filtered, washed with water and air-dried in a hood to give 287.6 g of crude product (theory 244.64 g). G.C. analysis (area percent) of the crude product using a 30-meter DB-1 capillary column and a program of 100–270° C. at 15° C./minute showed the material to consist of 93.4 percent dibromide (9.28 minutes retention time), 1.5 percent monobromide (5.46 minutes) and 1.3 percent tribromide (12.65 minutes). This material was used without purification in the next step of the process.

The next step of the process involved the in-situ preparation of the Bisoxime of 2,4,6-Trimethylisophthaldehyde from 1,3-Bis (Bromomethyl)-2,4,6-Trimethylbenzene by reactions that can be depicted as follows:

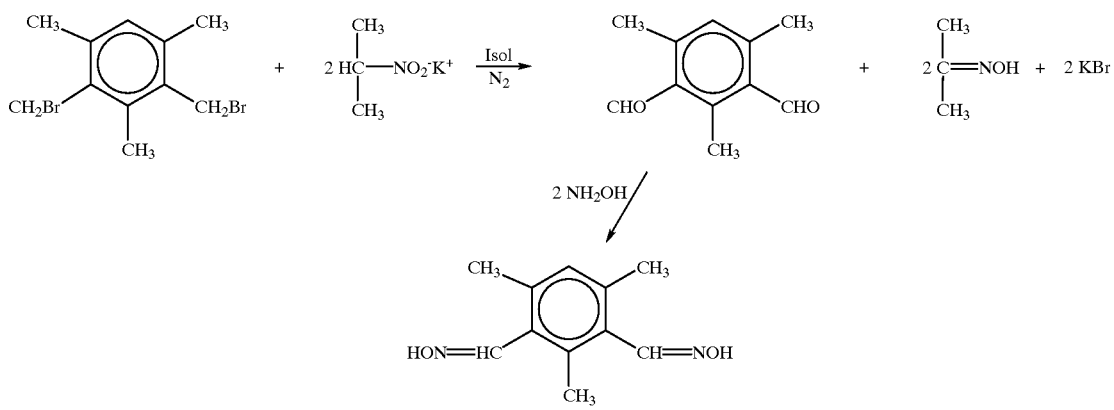

In conducting these reactions, a 5-liter three-necked round-bottomed flask equipped with a mechanical stirrer, condenser, pot thermometer and nitrogen inlet tube was charged with 118.56 g of 85 percent KOH pellets (1.8 moles), 1800 ml of isopropanol and 160.4 g (1.8 moles) of 2-nitroprpane (Aldrich). This mixture was then stirred under a slow nitrogen bleed until the potassium hydroxide (KOH) had essentially completely dissolved. This process takes approximately 30–45 minutes. During this period, the solution temperature gradually increases to about 38–40° C. At this point, 287.6 g (ca. 0.80 moles) of the crude dibromide was added to the solution all at once. The temperature of the mixture gradually increased to about 75–78° C. as the reaction proceeded before subsiding. After about 1.5 hours, the temperature had fallen to about 35–40° C. G.C. analysis of the mixture using the same column and conditions used for the dibromide showed it to be completely consumed. The major product peak for 2,4,6-Trimethylisophthaldehyde appears at 6.87 minutes retention time. Assuming complete conversion of dibromide to dialdehyde, 112.2 g of 50 percent aqueous hydroxylamine solution (ca. 1.7 moles) was then added to the mixture (at 45° C.) over about 5 minutes. The temperature of the mixture increased to about 51° C. After 1 hour, G.C. analysis showed no aldehyde peak at 6.87 minutes. The solution was then filtered to remove salts, such as potassium bromide (XBr). Salt cake was washed with 200 ml isopropanol and the filtrates combined. The alcohol solution was then poured into a large excess of stirred cold water to precipitate the crude oxime. After filtration and drying, 128.1 g was isolated. This represented a 77.7 percent yield.

In the final step of this procedure, Mesitylene Dinitrile Oxide was prepared by the reaction:

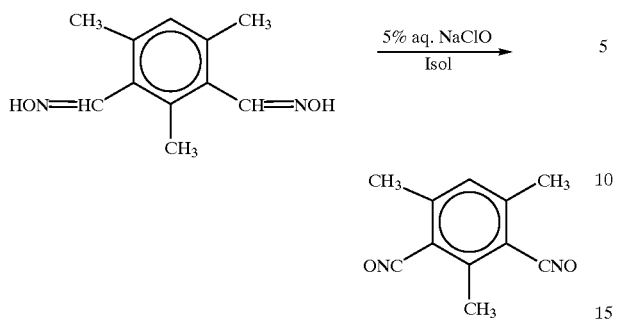

A mechanical stirrer with a stainless steel agitator blade was set up in a 5-liter stainless steel beaker. With stirring, 115.25 g (ca. 0.559 moles) of the crude bis-oxime was then dissolved in 2500 ml of isopropanol in the beaker. The beaker was placed in an ice water bath and the solution cooled to 10–15° C. Then, 1825 g (ca. 1.225 moles) of commercial bleach (ca. 5 percent NaClO) was slowly added dropwise to the stirred oxime solution over a 6-hour period. As the product MDNO formed, it precipitated from the isopropanol mixture. Ten minutes after all the 5 percent sodium hypochlorite has been added, the mixture was diluted with 4 liters of water and then filtered to remove the crude product. The product was air-dried to yield 98.0 g of a white solid having a melting point of 137–140° C. The FTIR spectra of this material shows a very sharp distinctive absorption band for the—CNO functionality at 2296 cm$^{-1}$.

EXAMPLE 2

In this experiment, mesitylene mononitrile oxide was synthesized from mesitylene. In the first step of the procedure, mesitylene was halomethylated to product 1-bromomethyl-2,14, 6-trimethylbenzene by a chemical reaction that can be depicted as follows:

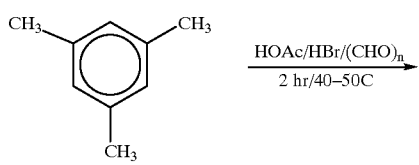

In the procedure used, a 500-ml three-necked round-bottomed flask equipped with a mechanical stirrer, pot thermometer and condenser was charged with 48.0 g (0.40 moles) of 98 percent pure mesitylene (Aldrich), 12.32 g (0.40 moles) of 95 percent paraformaldehyde (Aldrich), 200 ml of glacial acetic acid and 108.32 g (80 ml) or 0.414 moles of 30 percent HBr/HOAc solution (Aldrich). The mixture was heated at 40–50 with stirring for 2 hours. G.C. area percent analysis using the same column and conditions as the previous experiments indicated 95.2 percent monobromide with a retention time of 5.51 minutes and 2.2 percent dibromide with a retention time of 9.23 minutes. The reaction mixture was then poured into 500 ml of stirred cold water. Within a few minutes, a white solid crystalline product had solified. The product was filtered, washed with water and air-dried to give 76.48 g crude product; 89.7 percent yield. The crude material was subsequently used without purification in the synthesis of the monooxime.

In the next step, the oxime of 2,4,6-trimethylbenzaldehyde was prepared from 1-Bromomethyl-2,4,6-Trimethylbenzene by the following reactions:

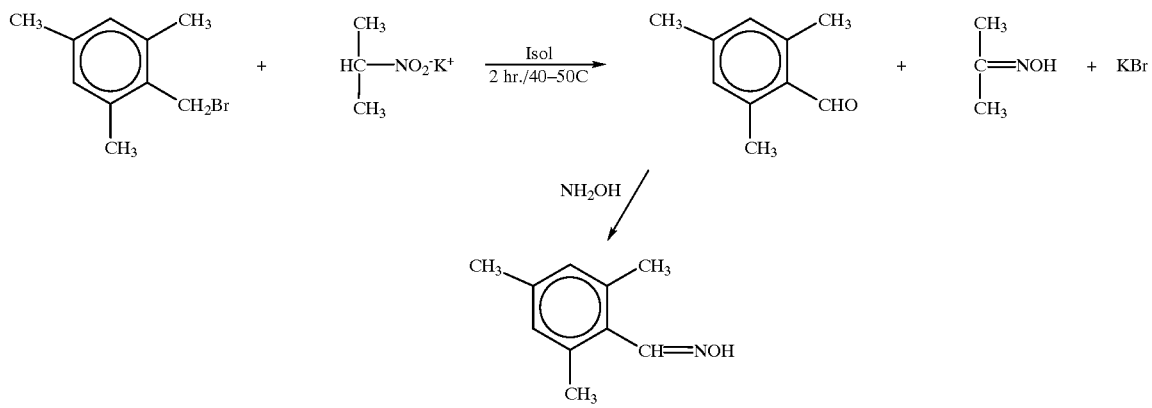

In the procedure used, 1-liter three-necked round-bottomed flask equipped with a mechanical stirrer, pot thermometer, condenser and nitrogen inlet tube was charged with 26.35 g (0.40 moles) of 85 percent KOH pellets, 400 ml of isopropanol and 35.64 (0.40 moles) of 2-nitropropane. The mixture was stirred under a slow nitrogen bleed until essentially all the KOH had dissolved (ca. 30 minutes). Once dissolved, 76.48 g (ca. 0.3587 moles) of crude 1-bromomethyl-2,4,6-trimethylbenzene from previous experiment, was added all at once. Temperature of reaction mixture slowly increased from 34 to 53° C. Temperature slowly subsided to room temperature over a 2-hour period. Mixture was then reheated to 70° C. and analyzed by G.C. using same column and conditions as with previously described experiments. G.C. analysis (area percent) shows 92 percent desired product (monoaldehyde with a retention time of 4.5 minutes and 2.2 percent dialdehyde at 6.85 minutes. To the warm solution was then added dropwise over 5 minutes 25.74 g (0.39 moles) of 50 percent aqueous hydroxylamine solution. After stirring 30 minutes at 50° C., G.C. analysis indicated that all the aldehyde had been converted to oxime. Retention time for the monooxime was 6.04 minutes. The reaction mixture was then poured into excess cold water to precipitate the oxime. The product was filtered, washed with water and air-dried to give 60.18 g of crude product as a white crystalline solid. The theoretical weight of the product produced was 58.5 grams.

Then, Mesitylene Mononitrile Oxide was synthesized by the following reaction:

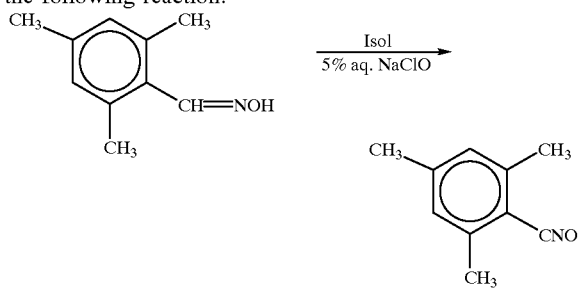

In the procedure utilized, 47.87 g (0.3055 moles) of the crude monooxime of 2,4,6-trimethylbenzaldehyde was dissolved in 1528 ml of isopropanol. The resulting stirred solution was then treated to the dropwise addition of 573 g (ca. 0.382 moles) of commercial 5 percent sodium hypochlorite solution over a 2-hour period at 10–15° C. Ten minutes after complete bleach addition, the mixture was diluted with excess water, filtered, washed with water and dried in air to give 50.0 g of product as an off-white solid; m.p. 105–108° C. G.C. area percent analysis of isolated product using same column and conditions as previously described showed a retention time of 6.31 minutes.

EXAMPLE 3

In this experiment, dinitrile oxides were prepared from a commercial source of divinylbenzene that contained m-divinyl-benzene, p-divinylbenzene, 1-ethyl-3-vinyl-benzene and 1-ethyl-4-vinylbenzene.

In the first step of the process, meta/para diethylbenzenes were prepared by the reaction:

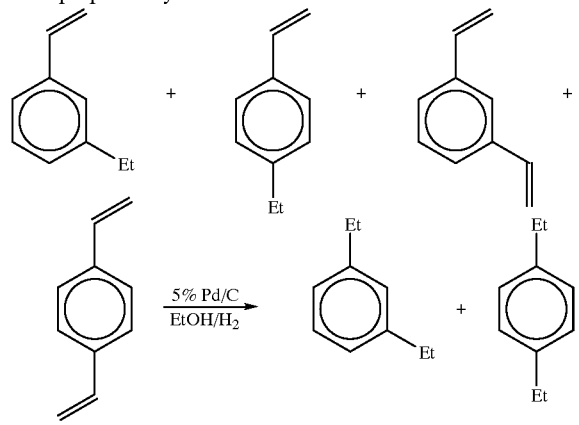

In carrying out this reaction, a 500 ml Parr hydrogenation bottle was charged with 0.5 g of 5 percent Pd/C catalyst followed by 200 ml of ethanol and 50.0 g (ca. 0.423 moles olefin) of the 55 percent commercial divinylbenzene (DVB). Then, the bottle was attached to Parr apparatus and briefly evacuate to remove air. Repressure to 45–50 psig with hydrogen. Upon shaking, the temperature of the reaction mixture increased from 75 to 170° F. over 25 minutes. Hydrogenation abruptly stopped after 48 pounds of hydrogen had been taken up. G.C. area percent analysis of starting material using a 30-meter DB-1 and 70° C. isothermal program indicated that the 55 percent DVB material actually consists of 32.7 percent 1-vinyl-3-ethylbenzene, 10.65 percent 1-vinyl-4-ethylbenzene, 38.15 percent 1,3-divinylbenzene and 17.25 percent 1,4-divinylbenzene. After hydrogenation, the product consists of 71.52 percent 1,3-diethylbenzene and 28.3 percent 1,4-diethylbenzene. After removal of the ethanol solvent, the crude product was used as raw material for the following chloromethylation reaction.

Then, Mixed Isomer Bis-(Chloromethyl)-Diethylbenzene was synthesized according to the reaction:

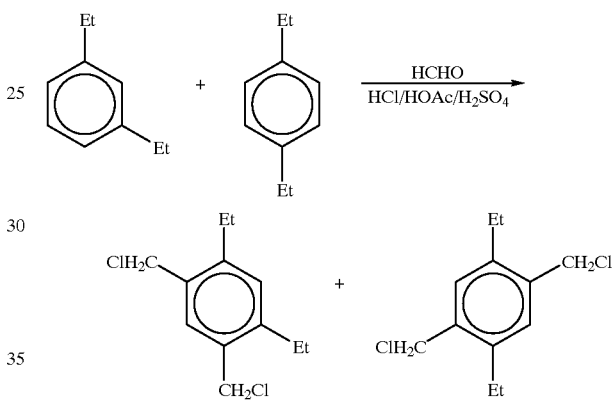

In conducting this reaction, a 1-liter three-necked round-bottomed flask equipped with mechanical stirrer, pot thermometer, condenser, dropping funnel and heating mantel was charged with 67.4 g (0.784 moles) of 35 percent aqueous formaldehyde solution, 81.8 g (69.8 ml) (0.784 moles) of conc. HCl, 33.0 g (31.4 ml) (0.55 moles) of glacial acetic acid and 35.2 g (0.2627 moles) of m/p-diethylbenzene. To this mixture add dropwise over 30 minutes, 180.4 g (100 ml) or (1.84 moles) of conc. sulfuric acid at 70–85° C. The temperature was then held constant for 4 hours. Analysis of mixture by G.C. showed 10 percent diethylbenzene, 55 percent monochloromethylated isomers and 28 percent dichloromethylated isomers at this stage. An additional 34.9 ml of conc. HCl and 15 g of 35 percent formaldehyde solution were then added and the mixture reluxed for an additional 3 hours. Analysis then showed 29 percent mono and 65 percent dichloromethylated products. After standing at room temperature overnight, a crystalline solid precipitated and was isolated by filtration, washed with hexane and dried to give 49.05 g product. G.C. analysis showed the material to be 93.1 percent dichloromethylated diethylbenzenes consisting mostly of one isomer.

Then, Bis-oximes of Diethylterephthalaldehyde were synthesized in situ from Bis-(Chloromethyl)-Diethylbenzenes according to the following reactions:

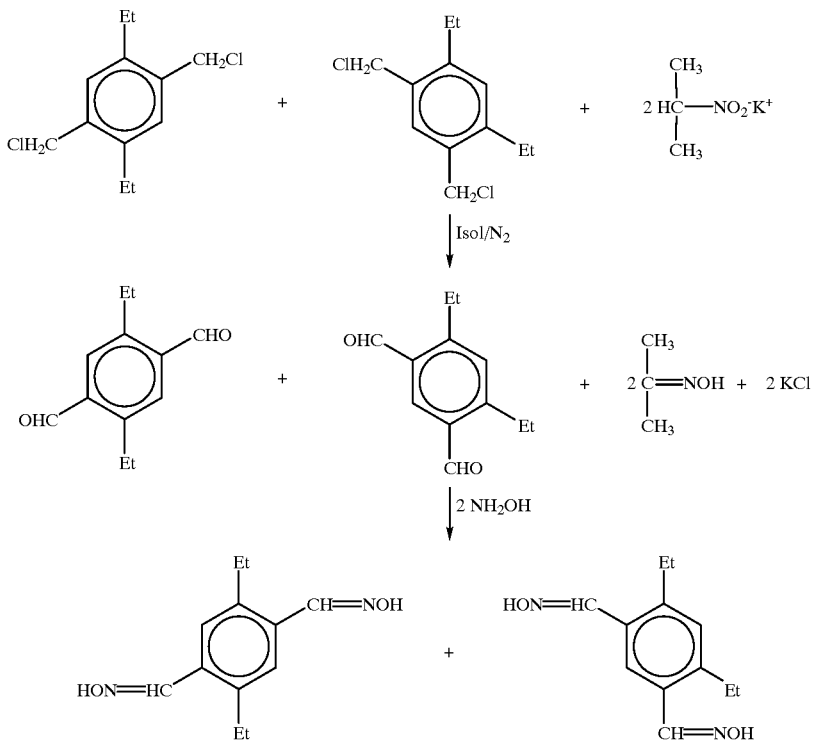

In the procedure used to carry out this reaction, a 1-liter three-necked round-bottomed flask equipped with a mechanical stirrer, not thermometer, condenser and nitrogen tube inlet was charged with 30.3 g (0.46 moles) of 85 percent KOH pellets, 450 ml isopropanol and 41.0 g (0.46 moles) of 2 nitropropane. The mixture was stirred under a slow nitrogen bleed for about 30 minutes until all the KOH had dissolved. The solution was warmed to about 50° C. and 49.0 g (0.213 moles) of the mixed isomers of bis-(chloromethyl)-diethylbenzene were added all at once. The temperature gradually increased to 68° C. After 1 hour, G.C. analysis indicated that no starting material remained. Two new aldehyde peaks were observed with retention times of 6.80 and 6.95 minutes with the DB-1 column and a program of 100–270° C. at 15° C./min. At 55°, 30.36 g (0.46 moles) of 50 percent aqueous hydroxylamine was added over about 10 minutes. The temperature increased to 67° C. After 30 minutes, G.C. analysis indicated that all the aldehyde isomers had been consumed. The warm reaction mixture was poured into excess cold water to solidify the product. The crude product was filtered, washed with water and air-dried to give 40.25 g of flesh-colored solid. Theoretical yield should be 46.86 g. The crude yield was 85.9 percent.

Dinitrile Oxides were then prepared from the Mixed Isomers of Diethylisophthaloaldehyde Dioximes. In the procedure used, mechanical stirrer with a stainless steel agitator blade was set up in a 2-liter stainless steel beaker. Then, 40.25 g (ca. 0.1829 moles) of the crude bis-oxime was then dissolved in 1000 ml of isopropanol in the beaker with stirring. The beaker was place in an ice water bath and the solution cooled to 10–15° C. Over a 2-hour period, 597 g (ca. 0.40 moles) of commercial bleach (ca. 5 percent NaClO) was then slowly added dropwise to the stirred oxime solution. As the product dinitrile oxide forms, it precipitates from the isopropanol mixture. Ten minutes after all the 5 percent sodium hypochlorite has been added, the mixture was diluted with 1 liter of water and then filtered to remove the crude product.

The product was air-dried to yield 31.6 g of a yellow-gold solid. The FTIR spectra of this material shows a very sharp distinctive absorption band for the —CNO functionality at 2285 cm$^{-1}$. Crude yield was determined to be 79.2 percent.

EXAMPLE 4

In this experiment, dinitrile oxides were synthesized from 1,2,4-Trimethylbenzene. In the first step of the experiment, bis-(bromomethyl)isomers of 1,2,4-trimethylbenzene were synthesized according to the reaction:

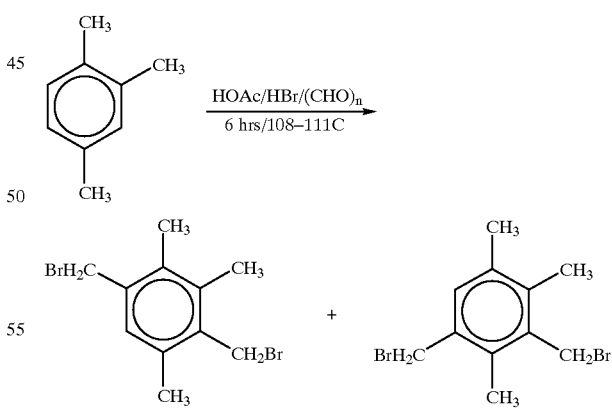

In the procedure used, a 1-liter three-necked round-bottomed flask equipped with a mechanical stirrer, condenser and pot thermometer was charged with 24.0 g (0.20 moles) of 1,2,4-trimethylbenzene (Aldrich), 20.65 g (ca. 0.655 moles) of 95 percent pure paraformaldehyde (Aldrich) and 178 g (131.5 ml) (0.655 moles) of 30 percent HBr in acetic acid solution (Aldrich). The mixture was slowly heated with stirring to ca. 80° C. where a mild exotherm was noted. Heating was discontinued while temperature rose to 85–90° C. After exotherm subsided, temperature was increased to 108–110° C. and held there for 6 hours.

The mixture was allowed to stand at room temperature overnight. The crystalline solid was then filtered off and washed with hexane and air-dried. G.C. analysis of the crude product using a 30-meter DB-1 capillary column and a program of 100–270° C. at 15° C./minute showed the material to consist of 84.0 percent dibromides (8.93 minute and 9.41 minute retention time), 6.0 percent monobromide (5.66 minutes) and 5.7 percent tribromide (12.36 minutes). This material was used without further purification in the next step of the process.

In the next step of the process, Bis-oximes of 1,2,4-Trimethylisophthalaldehyde were synthesized from Bis-(Bromomethyl)-1,2,4-trimethylbenzenes according to the following reactions:

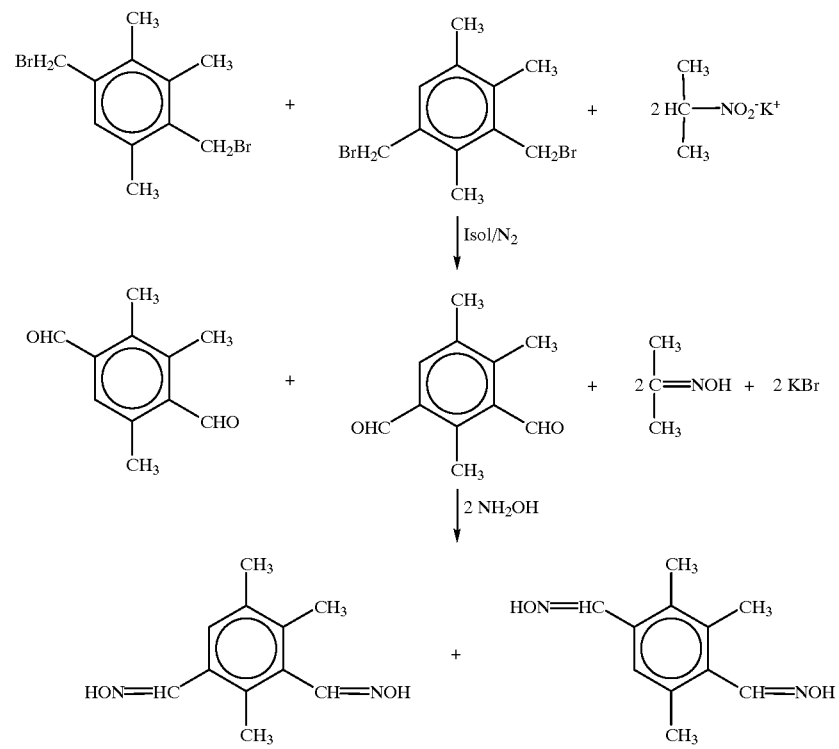

In the procedure used, a 1-liter three-necked round-bottomed flask equipped with a mechanical stirrer, pot thermometer, condenser and nitrogen tube inlet was charged with 28.33 g (0.43 moles) of 85 percent KOH pellets, 400 ml isopropanol and 39.2 g (0.44 moles) of 2 nitropropane. The mixture was stirred under a slow nitrogen bleed for about 30 minutes until all the KOH had dissolved. The solution was warmed to about 50° C. and 65.5 g (ca. 0.20 moles) (with regard to bromomethyl groups) of the mixed isomers of bis-(bromomethyl)-trimethylbenzene were added all at once. The temperature gradually increased to 75° C. After 1 hour at 70–75° C., G.C. analysis indicated that no starting material remained. One main aldehyde peak was observed with retention times of 7.02 minutes with the DB-1 column and a program of 100–270° C. at 15°C/minute. At 60° C., 28.38 g (0.43 moles) of 50 percent aqueous hydroxylamine was added over about 10 minutes. After about 1.5 hours, the mixture was poured into excess cold water to produce a brown and white sticky semi-solid. The semi-solid was filtered off and let stand for 1 week in the hood to solidify. The product was then recrystallized from a 50/50 isol/water mixture to isolate after filtering and drying, 25.1 g of product. This material was used in the next step of the experiment. The theoretical yield attained as 60.9 percent.

Then, Dinitrile Oxides were prepared From the Mixed Isomers of 1,2,4-Trimethyl-isophthaloaldehyde Dioximes which had been synthesized according to the reaction:

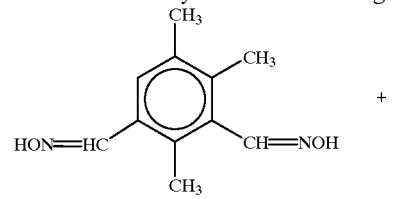

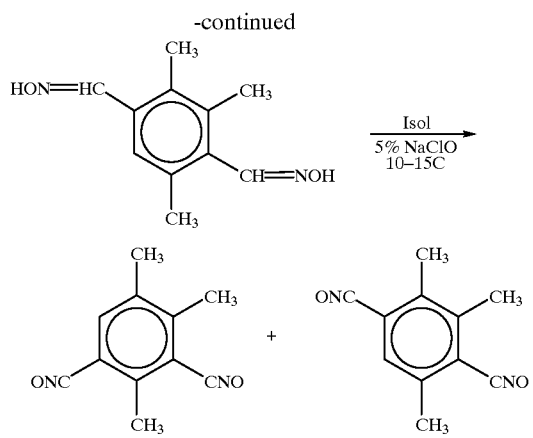

In the procedure used, a mechanical stirrer with a stainless steel agitator blade was set up in a 2-liter stainless steel beaker. Then, 25.1 g (ca. 0.1218 moles) of the crude bis-oxime was dissolved in 667 ml of isopropanol in the beaker with stirring. The beaker was placed in an ice water bath and the solution cooled to 10–15° C. Over a 2-hour period, 400 g (ca. 0.40 moles) of commercial bleach (ca. 5 percent NaClO) was then slowly added dropwise to the stirred oxime solution. As the product dinitrile oxide forms, it precipitates from the isopropanol mixture. Ten minutes after all the 5 percent sodium hypochlorite has been added, the mixture was diluted with 1 liter of water and then filtered to remove the crude product.

The product was air-dried to yield 19.13 g of a yellow solid. The FTIR spectra of this material shows a very sharp distinctive absorption band for the —CNO functionality at 2285 cm$^{-1}$. The crude yield attained was 77.0 percent.

While certain representative embodiments and details have been shown for the purpose of illustrating the subject invention, it will be apparent to those skilled in this art that various changes and modifications can be made therein without departing from the scope of the subject invention.

What is claimed is:

1. A process for the synthesis of stable aryl nitrile oxides which comprises the sequential steps of (1) halomethylating a halomethyl group onto a substituted aromatic compound having at least one substituent group selected from the group consisting of alkyl groups, aryl groups, fused aryl groups, alkaryl groups, halogen atoms, alkoxy groups and nitro groups, wherein said halomethyl group is halomethylated onto a position that is ortho to at least one of the substituent groups on the substituted aromatic compound to produce an ortho halomethylated-substituted aromatic compound, wherein the substituted aromatic compound is halomethylated by allowing the substituted aromatic compound to react with a mixture of acetic acid, hydrogen bromide, and paraformaldehyde; (2) conveying the ortho halomethylated-substituted aromatic compound into an ortho-substituted aromatic aldehyde by reacting the ortho halomethylated-substituted aromatic compound with a salt selected from the group consisting of sodium 2-nitropropane and potassium 2-nitropropane in a lower alcohol solvent; (3) converting the ortho-substituted aromatic aldehyde into an ortho-substituted aromatic oxime by reacting the ortho-substituted aromatic aldehyde with hydroxylamine; and (4) converting the ortho-substituted aromatic oxime into the ortho-substituted aryl nitrile oxide by reacting the ortho-substituted aromatic oxime with an aqueous sodium hypochlorite solution at a temperature which is within the range of about −5° C. to about 20° C.

2. A process as specified in claim 1 wherein the substituted aromatic compound is selected from the group consisting of 1,3,5-trimethylbenzene (mesitylene), 1,2,4,5-tetramethylbenzene (durene), toluene, o-xylene, m-xylene, p-xylene, pseudocumene, isodurene, prehnitene, 1,3-dimethyl-5-t-butylbenzene, 1,3,5-triethylbenzene, 1,3,5-tripropylbenzene, naphthalene, anthracene, α-methylnaphthalene, β-methylnaphthalene, phenanthrene, 1,2-benzanthracene, p-dichlorobenzene, o-chlorotoluene, p-chlorotoluene, p-bromotoluene, bromodurene, bromoisodurene, bromoprehnitene, bromomesitylene, 1-chloro-1-mesitylethylene, p-bromoethylbenzene, 1-chloro-1-mesitylpropene, α-chloroisodurene, p-nitrotoluene, 1-nitronaphthalene, 1,4-diethoxybenzene, 1-ethoxy-4-nitronaphthalene, 1,4-dipropoxybenzene, 1,4-dibutoxybenzene, 1,4-diamyloxybenzene, 2,5-dimethoxytoluene, 2,5-dimethoxyoctylbenzene, 2,5-dimethoxybromobenzene, 3,-chloromethyl-1,2-dimethoxybenzene, 4-(β-chloropropyl)-1,2-dimethoxybenzene, 2,3,4-trimethoxybromobenzene, trimethoxy-p-xylene and 5-propyl-1:3-benzodioxole.

3. A process as specified in claim 1 wherein the substituted aromatic compound is mesitylene.

4. A process as specified in claim 1 wherein the substituted aromatic compound is durene.

5. A process as specified in claim 2 wherein step (4) is carried out at a temperature which is within the range of about 0° C. to 15° C.

6. A process as specified in claim 1 wherein the substituted aromatic compound is halomethylated in step (1) at a temperature which is within the range of about 50° C. to about 120° C.

7. A process as specified in claim 1 wherein the substituted aromatic compound is halomethylated in step (1) at a temperature which is within the range of about 80° C. to about 95° C.

8. A process as specified in claim 2 wherein the salt utilized in step (2) is the sodium salt of 2-nitropropane.

9. A process as specified in claim 2 wherein the salt utilized in step (2) is the potassium salt of 2-nitropropane.

10. A process as specified in claim 2 wherein the aqueous sodium hypochlorite solution utilized in step (4) contains from about 4 weight percent to about 6 weight percent sodium hypochlorite.

11. A process as specified in claim 2 wherein the lower alcohol solvent utilized in step (2) contains from 1 to 5 carbon atoms.

12. A process as specified in claim 11 wherein the lower alcohol solvent utilized in step (2) is selected from the group consisting of methanol, ethanol, n-propyl alcohol, isopropyl alcohol, n-butyl alcohol, isobutyl alcohol and t-butyl alcohol.

13. A process as specified in claim 11 wherein step (2) is carried out at a temperature which is within the range of about 20° C. to about 100° C.

14. A process as specified in claim 11 wherein step (2) is carried out at a temperature which is within the range of about 30° C. to about 70° C.

15. A process as specified in claim 12 wherein step (2) is carried out at a temperature which is within the range of about 35° C. to about 55° C.

16. A process as specified in claim 2 wherein step (3) is carried out at a temperature which is within the range of about 20° C. to about 100° C.

17. A process as specified in claim 2 wherein step (3) is carried out at a temperature which is within the range of about 30° C. to about 70° C.

18. A process as specified in claim 2 wherein step (3) is carried out at a temperature which is within the range of about 35° C. to about 55° C.

* * * * *